US006637366B1

(12) United States Patent
Bedding et al.

(10) Patent No.: US 6,637,366 B1
(45) Date of Patent: Oct. 28, 2003

(54) NEMATODE BIOPESTICIDE

(75) Inventors: Robin Anthony Bedding, Cook (AU); Simone Daniella Clark, Conder (AU); Karen Louise Butler, Ainslie (AU); Jacqueline Louise Vella, Flynn (AU); Felice Driver, Pyrmont (AU)

(73) Assignee: Commonwealth Scientific and Industrial Research Organization, Campbell (AU)

( * ) Notice: Subject to any disclaimer, the term of this patent is extended or adjusted under 35 U.S.C. 154(b) by 0 days.

(21) Appl. No.: 09/869,080

(22) PCT Filed: Dec. 23, 1999

(86) PCT No.: PCT/AU99/01152

§ 371 (c)(1),
(2), (4) Date: Oct. 1, 2001

(87) PCT Pub. No.: WO00/38510

PCT Pub. Date: Jul. 6, 2000

(30) Foreign Application Priority Data

Dec. 24, 1998 (AU) ................................. PP7927

(51) Int. Cl.$^7$ .......................... A01K 29/00; C11D 3/00; C09D 5/14
(52) U.S. Cl. ...................... 119/6.7; 510/302; 106/15.05
(58) Field of Search .................. 119/6.5, 6.7; 510/302; 106/15.05

(56) References Cited

FOREIGN PATENT DOCUMENTS

AU 33839/93 9/1993

OTHER PUBLICATIONS

Villani, M.G. et al., "*Entomogenous Nematodes as Biological Control Agents of European Chafer and Japanese Beetle (Coleoptera: Scarabaeidae) Larvae Infesting Turfgrass*", Journal of Economic Entomology, vol. 81(2), pp. 484–487, Apr. 1988.

Forschler, B.T. et al., "*Field Efficacy and Persistence of Engomogenous Nematodes in the Management of White Grubs (Coleoptera: Scarabaeidae) in Turf and Pasture*", Journal of Economic Entomology, vol. 84(5), pp. 1454–1459, Oct. 1991.

Forschler, B.T. et al., "*Concentration–Mortality Response of Phyllophaga hirticula (Coleoptera: Scarabaeidae) to Three Entomogenous Nematodes*", Journal of Economic Entomology, vol. 84(3), Jun. 1991.

Alm, S.R. et al., "*Biological Control of Japanese, Oriental, and Black Turfgrass Ataenius Beetle (Coleoptera: Scarabaeidae) Larvae with Entomopathogenic Nematodes (Nematoda: Steinernematidae, Heterorhabditidae)*", Journal of Economic Entomology, vol. 85(5), pp. 1660–1605, Oct. 1992.

Foschler, B.T. et al., "*Parasitism of Phyllophaga hirticula (Coleoptera: Scarabaeidae) by Heterorhabditis Heliothidis and Steinernema carpocapsae*", Journal of Invertibrate Pathology, vol. 58(3), pp. 396–407, Nov. 1991.

Theunis, W., "*Susceptibility of the taro beetle, papuana uninodis, to entomopathogenic nematodes*", International Journal of Pest Management, vol. 44(3), pp. 139–143, Sep. 1998.

Lei, Z. et al., "*Heterorhabditid Behavior in the Presence of the Cabbage Maggot, Delia radicum, and its Host Plants*", Journal of Nematology, vol. 24(1), pp. 9–15, Mar. 1992.

Shetlar, D.J et al., "*Irrigation and use of Entomogenous Nematodes, Neoplectana spp. And Heterohabditis heliothidis (Rhabditida: Steinernematidae and Heterohabditidae), for control of Japanese Beetle (Coleoptera: Scarabaeidae) Grubs in Turfgrass*", Journal of Economic Entomology, vol. 81(5), pp. 1318–1322, Oct. 1988.

Kard, B.M.R. et al., "*Field Suppression of Three White Grub Species (Coleoptera: Scarabaeidae) by the Entomogenous Nematodes Steinernema feltiae and Heterorhabditis heliothidis*", Journal of Economic Entomology, vol. 81(4), pp. 1033–1039, Aug. 1988.

Wright, R.J. et al., "*Steinernematid and Heterorhabditid Nematodes for Control of Larval European Chafers and Japanese Beetles (Coleoptera: Scarabaeidae) in Potted Yew*", Journal of Economic Entomology, vol. 81(1), pp. 152–157, Feb. 1988.

Primary Examiner—Anne-Marie Falk
Assistant Examiner—Celine Qian
(74) Attorney, Agent, or Firm—McDermott, Will & Emery

(57) ABSTRACT

A composition and method for controlling scarabs, especially lawn scarabs, utilising certain strains of the entomopathogenic nematode species, *Heterorhabditis zealandica* are disclosed. The nematode strains used in the composition and method generally have an $LD_{50}$ value of less than 300 IJ as measured by pot assays against final instar scarab larvae.

19 Claims, 10 Drawing Sheets

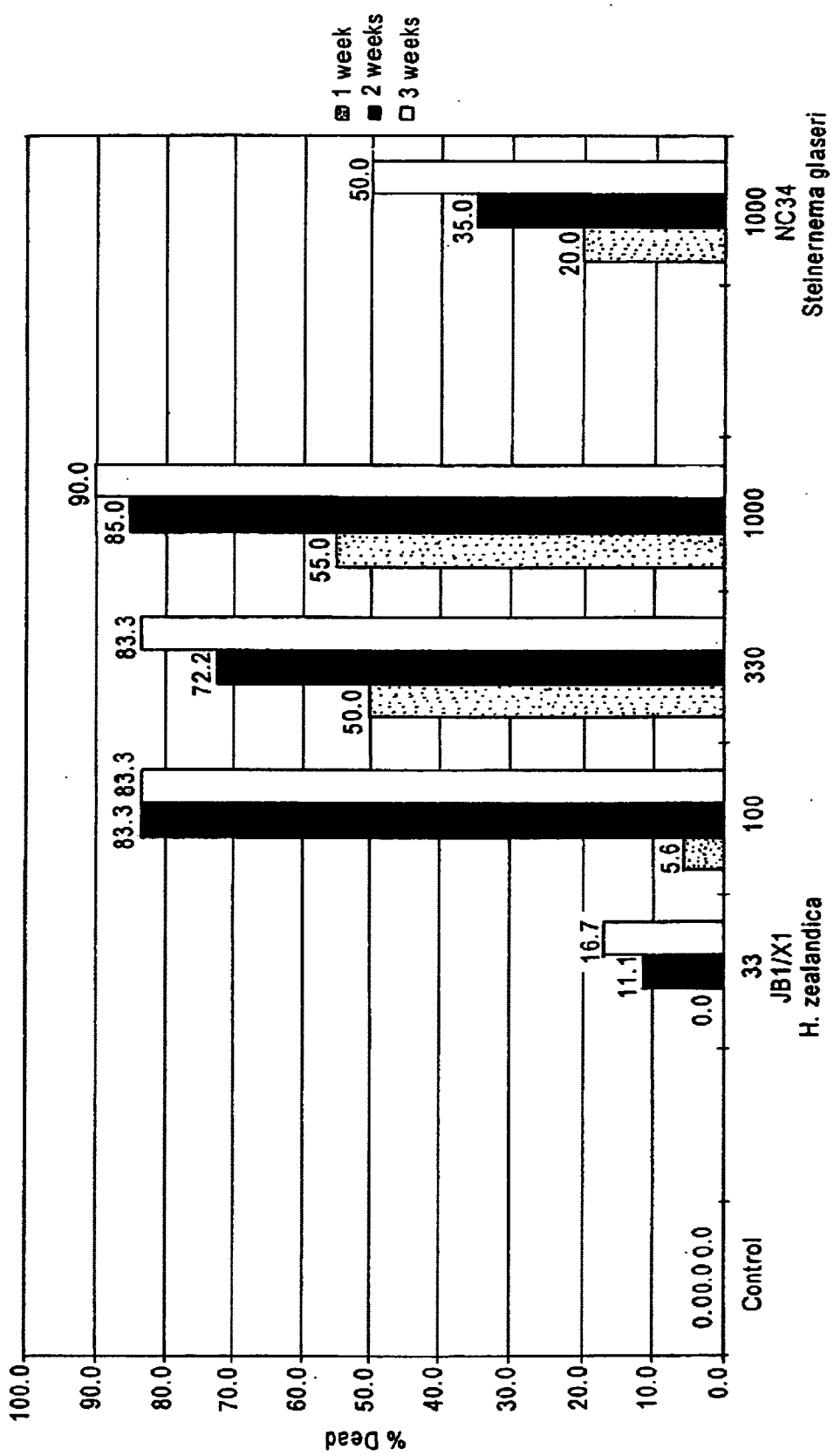

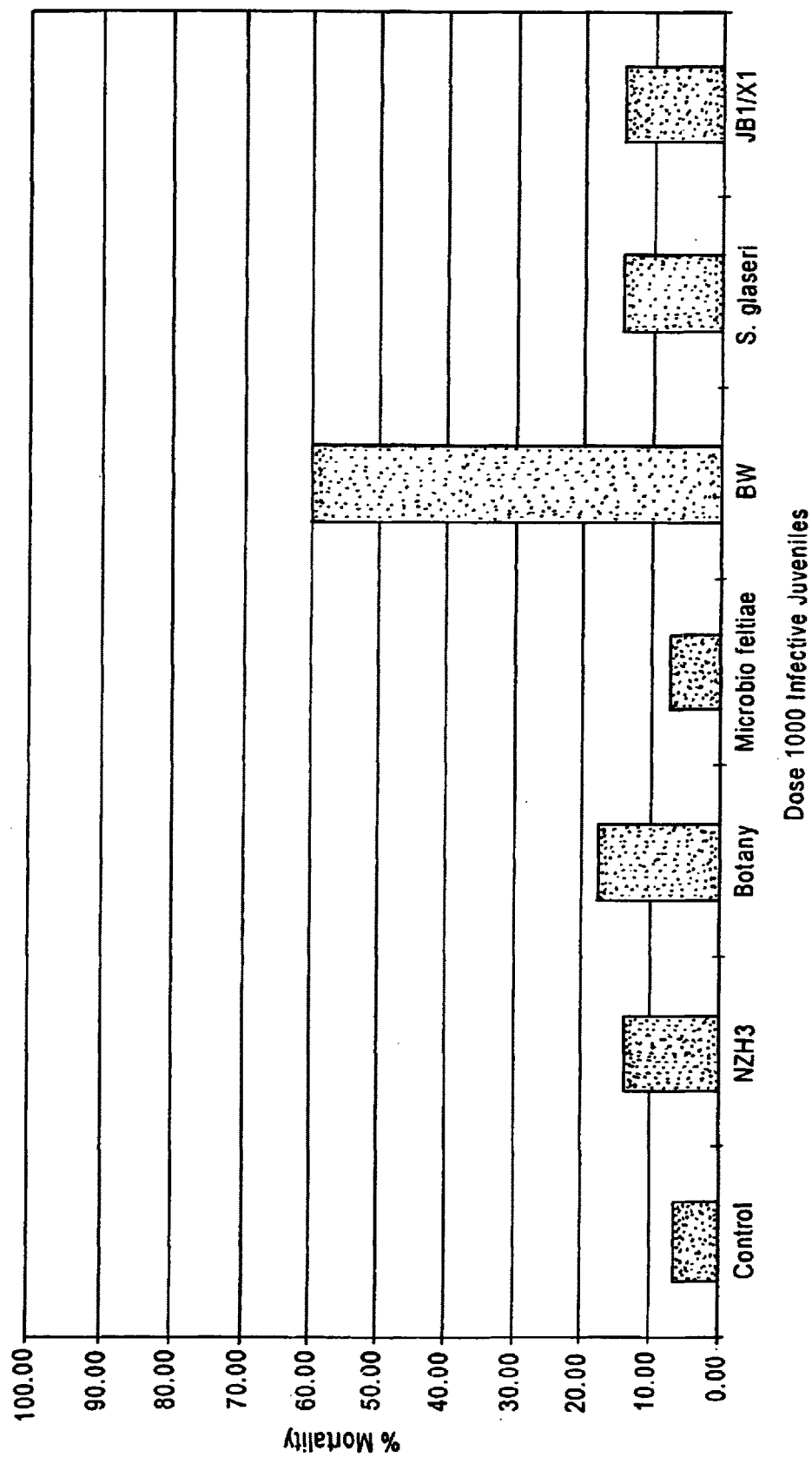

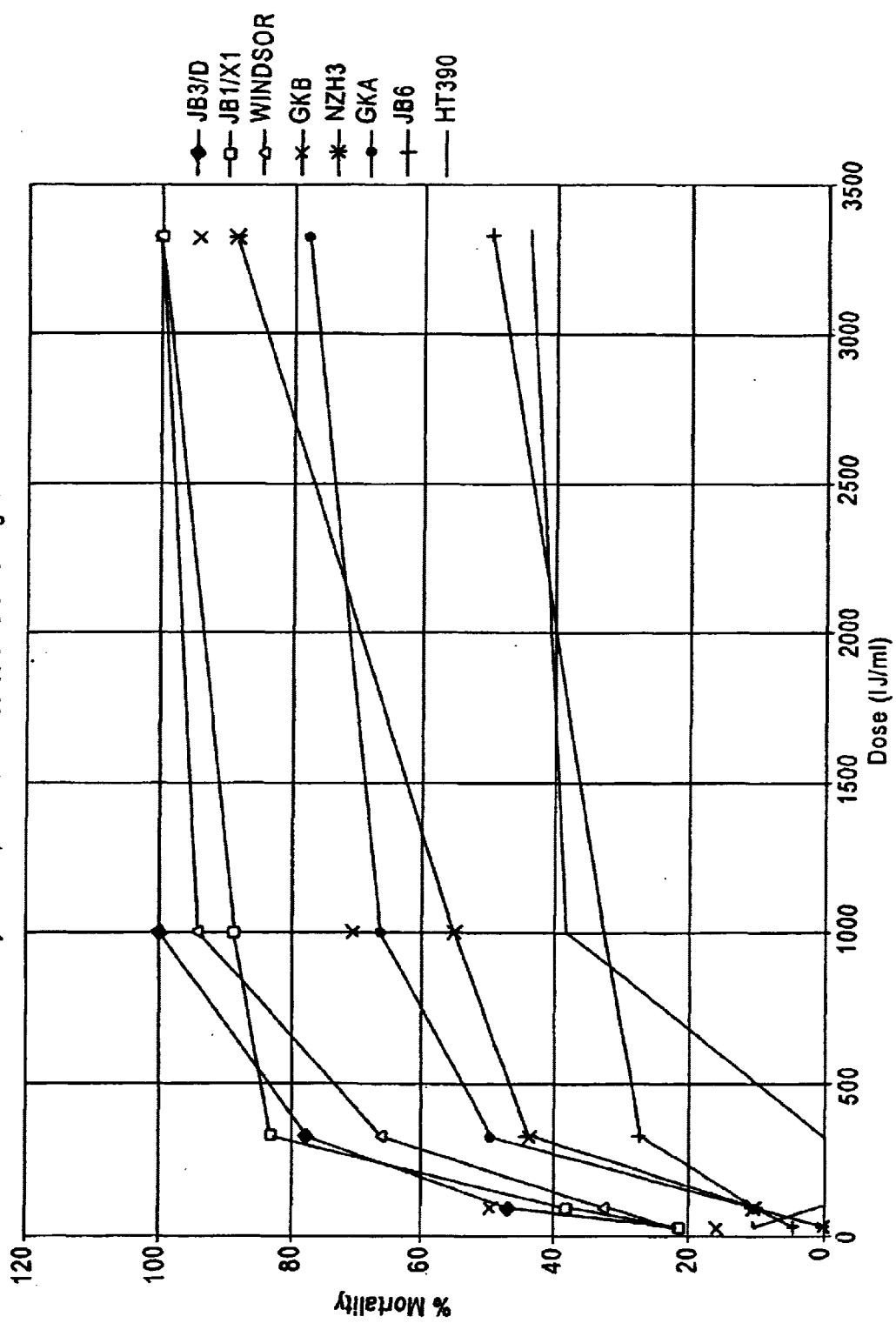

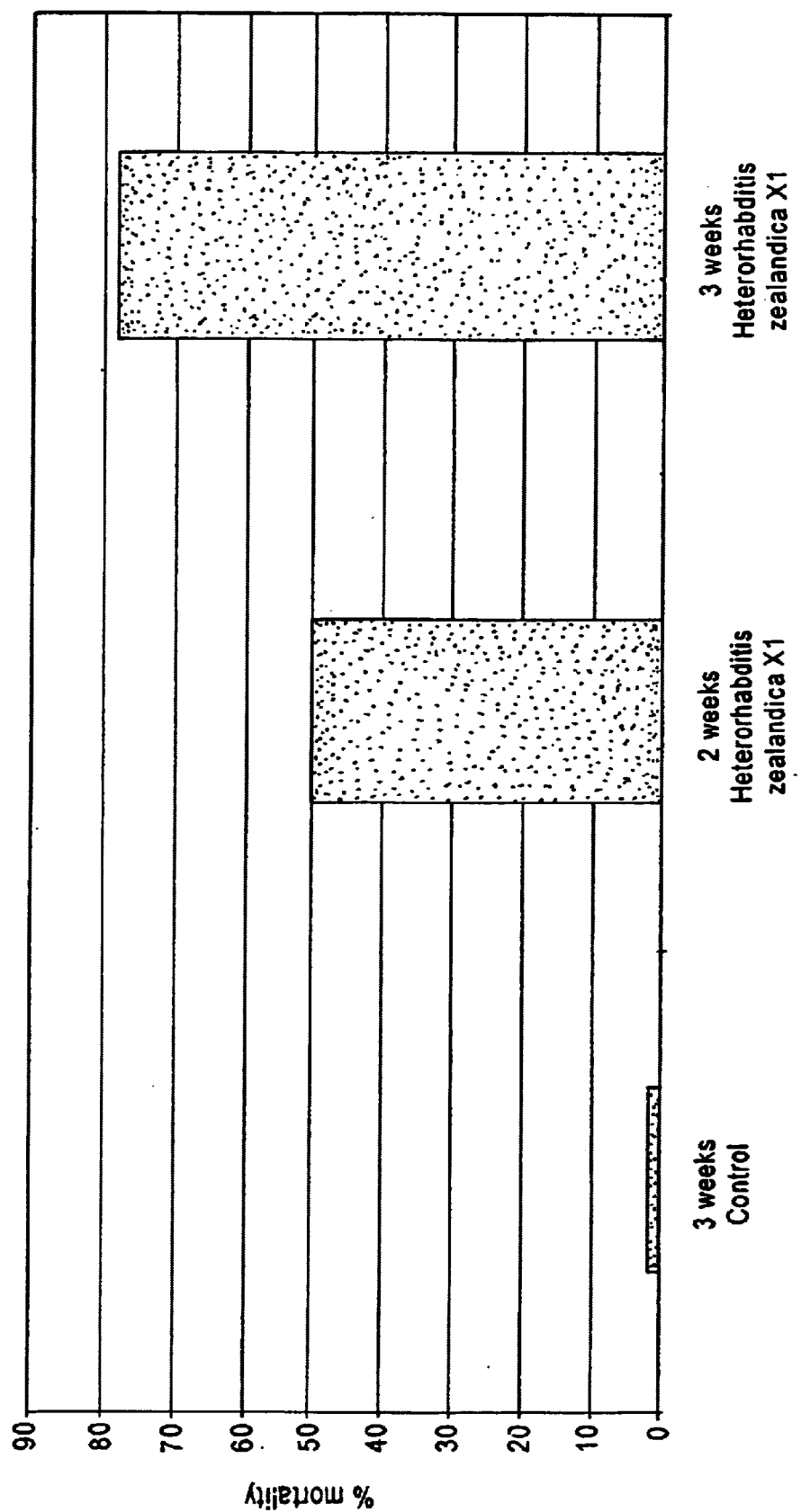

NEMATODE BIOPESTICIDE

FIELD OF THE INVENTION

Figure 1:
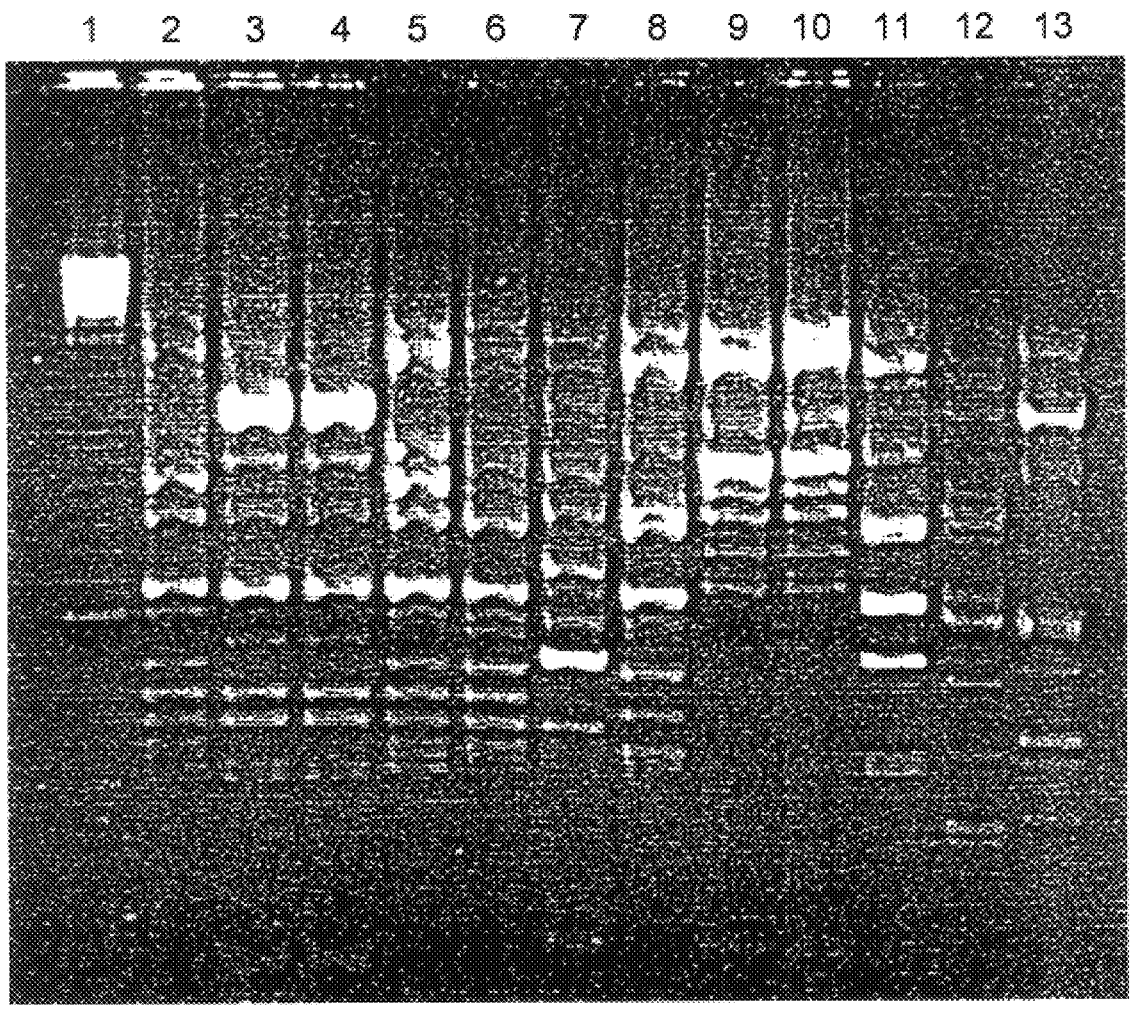

The present invention relates to a composition and method for controlling scarabs, especially lawn scarabs, utilising certain strains of the entomopathogenic nematode species *Heterorhabditis zealandica*.

BACKGROUND OF THE INVENTION

The family of beetles known as Scarabaeidae includes a number of species that are known as significant agricultural and horticultural pests. Larvae of lawn scarabs (such as *Cyclocephala signaticollis, Heteronychus arator, Adoryphorus couloni, Antitrogus morbillosus, Anoplognathus porosus, Ataenius imparalis, Sericesthis geminata, S. pruinosus, S. nigrolineata, Scityla sericans, Saulostomus villosus, Aphodius tasmaniae,* Heteronyx spp, *Rhopoea magnicornis, Popillia japonica, Cyclocephala borealis, C. hirta, C. parallela, Melolontha melolontha, Anomala aenea, Phyllophaga phyllophaga, P. hirticula, Plyllopertha horticola, Haplididia etrusca, Maladea matrida, Costelytra zealandica, Amphimallon solstatialis,* and *Ligyrus subtropicus*) feed on the roots of grasses thereby causing considerable damage to pastures, lawns and anmenity turf. Control treatments typically involve the use of chemical pesticide sprays, however these have a number of disadvantages. including low efficacy (particularly against final instar larvae), low specificity and public concern regarding pesticide residues. Consequently, there is a need for a viable alternative to the control of lawn scarabs by chemical pesticide spraying. In this regard, the present inventors have identified certain strains of the entomopatliogenic nematode species *H. zealandica* that are suitable for use as biological control agents for lawn scarabs.

DISCLOSURE OF THE INVENTION

Thus, in a first aspect, the present invention provides a composition for controlling a population of larval and/or pupal scarabs, comprising an amount of an entomopathogenic nematode optionally in admixture with a suitable agricultural and/or horticultural carrier, wherein said entomopathogenic nematode belongs to the species *Heterorhabditis zealandica* and has an LD50 value of less than 300 infective juveniles (IJ) as measured by pot assays against final instar scarab larvae.

Preferably, the entomopathogeniic nematode belongs to a strain of *H. zealandica* which has an LD50 value of less than 300 IJ as measured by pot assays against final instar *Cyclocephlala signaticollis* larvae and/or final instar *Popillia japonica* larvae.

More preferably, the entomopathogenic nematode belongs to a strain of *H. zealandica* which has an LD50 value of less than 175 IJ against final instar *C. signaticollis* larvae and/or final instar *P. japonica* larvae. Especially preferred are the strains designated JB1/X1, GKB and JB3D.

Compositions will include an amount of the entomopathogenic nematode which is, typically, about 50 to 10,000, more preferably about 500 to 1000, IJ/ml of composition.

Compositions will also typically include a suitable agricultural and/or horticultural carrier. Where the composition is desired to be in the form of an aqueous spray, the carrier may be selected from, for example, water or solutions in water of polyethylene glycol or glycerol or small quantities of wetting agent or various substances to stimulate nematode activity such as citric acid, insect blood or low concentrations of chemical pesticide. Where the composition is desired to be in a solid form, the carrier may be selected from, for example, calcium alginate and polyacrylamide (as would be suitable for gelled pellets), attapulgite or vermiculite (as would be suitable for solid granules), or other moist substrates such as peat, sponge, sawdust or cellulose. Compositions in solid form may be dispersed into an aqueous carrier (such as those mentioned above) for use as an aqueous spray.

Compositions are preferably stored at low temperature (e.g. 2 to 10° C.) under aerobic conditions, and at a water activity of abpout $A_w$ 0.97.

In a second aspect, the present invention provides a method for controlling a population of larval and/or pupal scarabs in an affected area, said method comprising applying to said area a composition in accordance with the first aspect.

For compositions in the form of aqueous sprays, application may be carried out with typical agricultural and/or horticultural spraying equipment including pressurised, fan sprayers venturi sprays and boom sprayers. For compositions to be applied in a solid form, application may be carried out with typical agricultural and/or horticultural scattering equipment such as those used for spreading fertilisers on lawn.

The composition will typically be applied to an affected area which has been subjected to heavy watering in amounts sufficient to provide 50,000 to 1 million $IJ/m^2$, nmore preferably 100,000 to 500,000 $IJ/m^2$. Following application, it is also preferable to submit the affected area once again to heavy watering in order to soak the composition into the root zone where the larval scarabs feed. Application of the composition is preferably conducted at dusk.

The composition and method of the invention may be used for the control of lawn scarabs (such as those mentioned above) and other pest scarabs (e.g. sugar cane scarabs, blueberry scarabs, etc.)

In a further aspect, the present invention provides a nematode, in a substantially purified form, selected from the *H. zealandica* strains designated JB1/X1, GKB and JB3D.

The term "controlling" as used herein in relation to a population of larval and/or pupal scarabs, is intended to refer to both maintaining (i.e. preventing increases) and reducing said population.

The terms "comprise", "comprises" and "comprising" as used throughout the specification are intended to refer to the inclusion of a stated step, component or feature or group of steps, components or features with or without the inclusion of a further step, component or feature or group of steps, components or features.

The invention will hereinafter be described with reference to the following non-limiting examples and accompanying figures.

BRIEF DESCRIPTION OF THE ACCOMPANYING FIGURES

FIG. 1 shows a RAPD gel conducted on DNA from *H. zealandica* and other comparative strains. The primer used was OP-A04: 5'-AATCGGGCTG-3' (SEQ ID NO:1) (Operon Technologies Inc.). (Key: 1. 100 bp DNA Ladder; 2. *H. zealandica* (Great Keppel A); 3. *H. zealandica* (Great Keppel B); 4. *H. zealandica* (Great Keppel C); 5. *H. zealandica* (Windsor); 6. *H. zealandica* (NZH3); 7. *H.* zealandica (WA Het); 8. Heterorhabditis sp. (JB6); 9. *H. zealandica* (JB3D); 10. *H. zealandica* (JBX1); 11. Heterorhabditis sp. (HT390); 12. *H. megidis* (Microbio); 13. *H. bacteriophera* (NJ)).

Figure 2:
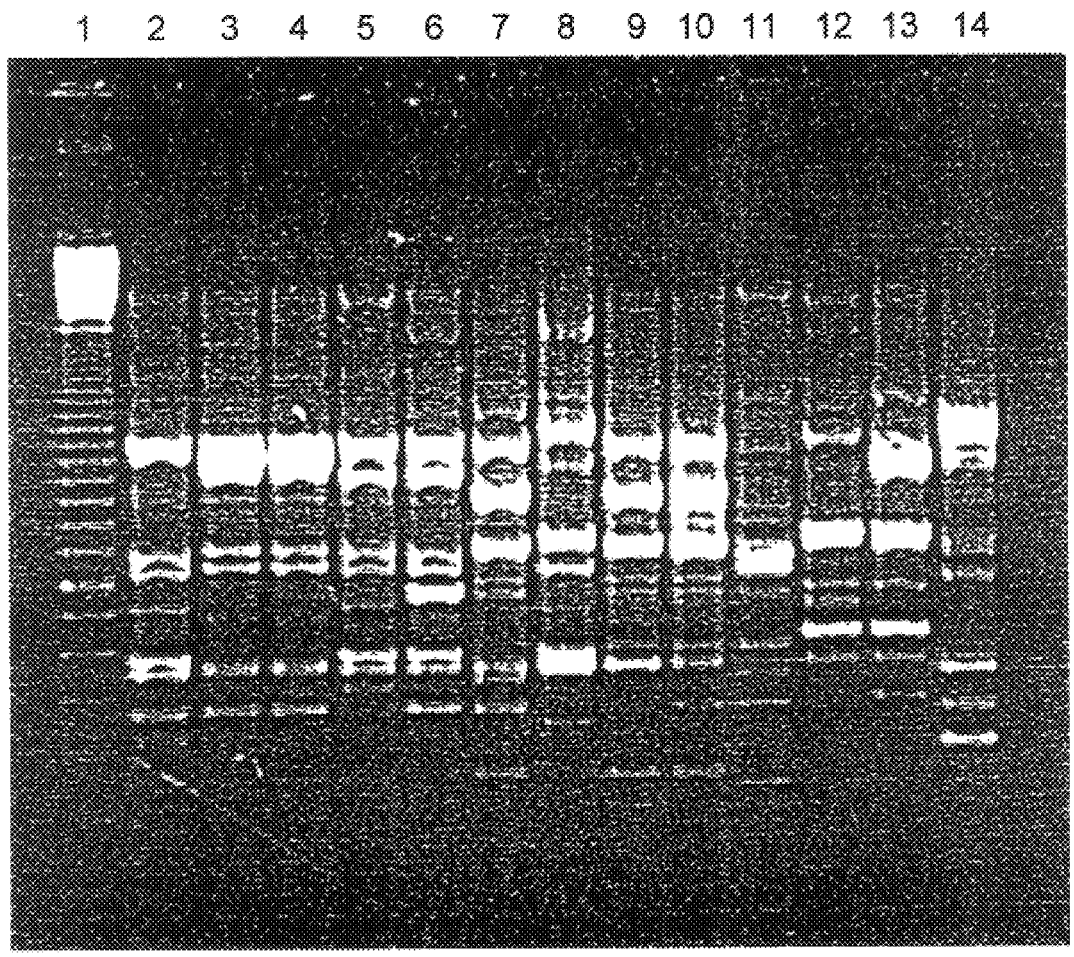

FIG. 2 shows a RAPD gel conducted on DNA from *H. zealandica* and other comparative strains. The primer used was OP-F03: 5'-CCTGATCACC-3' (SEQ ID NO:2) (Operon Technologies Inc.). (Key: 1. 100 bp DiNA Ladder; 2. *H. zealandica* (Great Keppel A); 3. *H. zealandica* (Great Keppel B); 4. *H. zealandica* (Great Keppel C); 5. *H. zealandica* (Windsor); 6. *H. zealandica* (NZH3); 7. *H. zealandica* (WA Het); 8. Heterorhabditis sp. (JB6); 9. *H. zealandica* (JB3D); 10. *H. zealandica* (JBX1); 11. Heterorhabditis sp. (HT390); 12. *H. megidis* (Microbio); 13. Heterorhabditis sp. (M145); 14. *H. bacteriophera* (NJ)).

Figure 3:
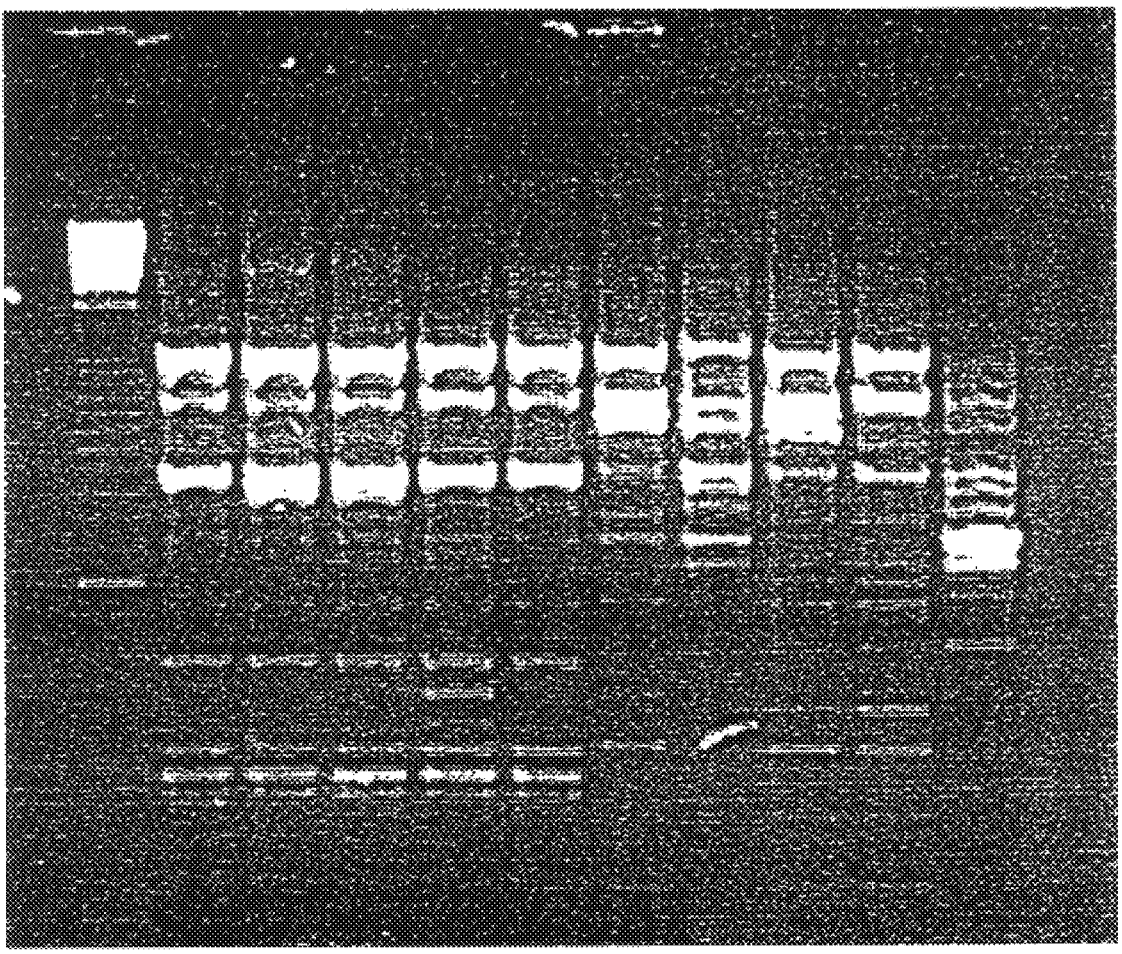

FIG. 3 shows a RAPD gel conducted on DNA from *H. zealandica* and other comparative strains. The primer used was OP-X11: 5'-GGAGCCTCAG-3'(SEQ ID NO3) (Operon Technologies Inc.). (Key: 1. 100 bp DNA Ladder; 2. *H. zealandica* (Great Keppel A); 3. *H. zealandica* (Great Keppel B); 4. *H. zealandica* (Great Keppel C); 5. *H. zealandica* (Windsor); 6. *H. zealandica* (NZH3); 7. *H. zealandica* (WA Het); 8. Heterorhabditis sp. (JB6); 9. *H. zealandica* (JB3D); 10. *H. zealandica* (JBX1); 11. Heterorhabditis sp. (HT390)).

Figure 4:
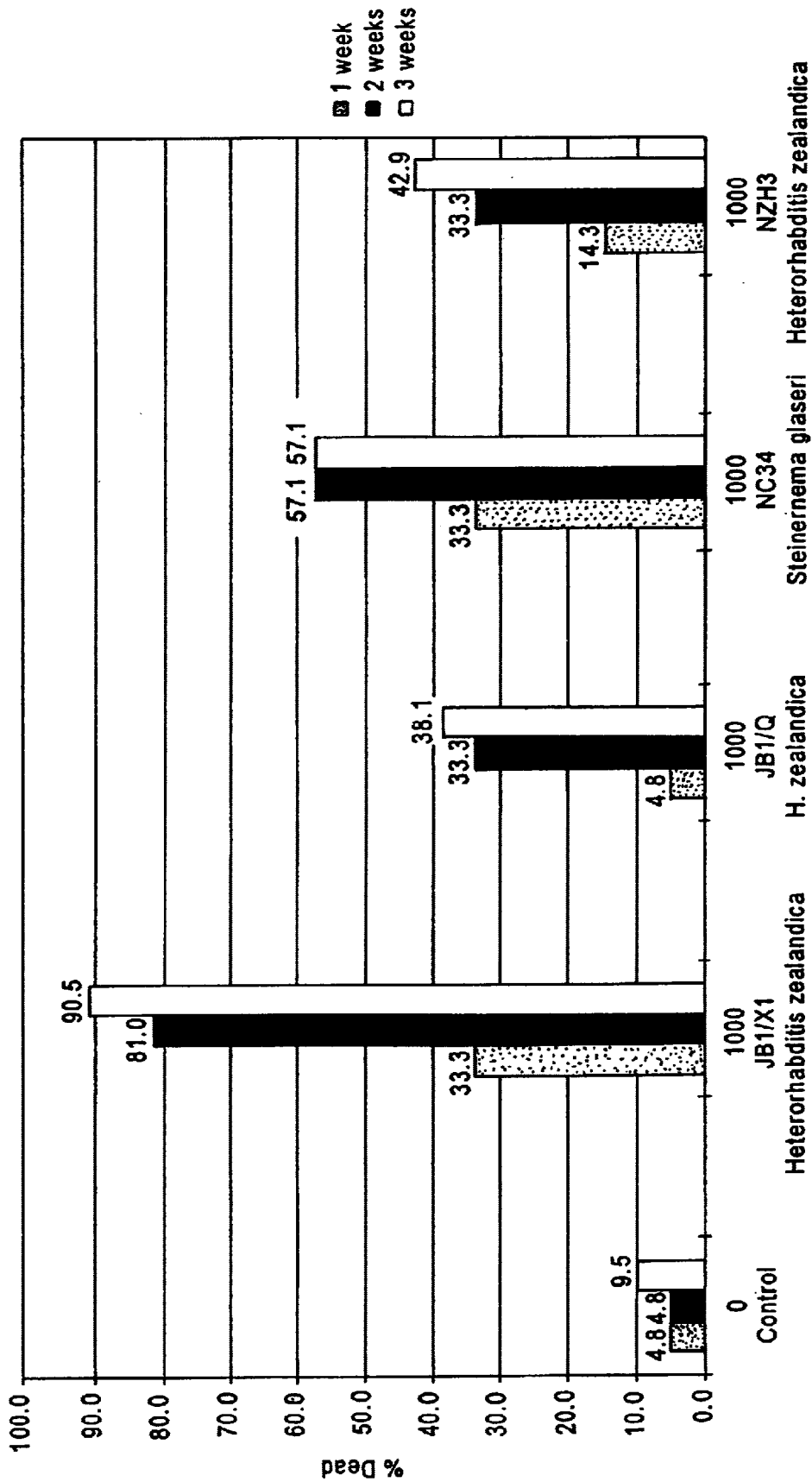

FIG. 4 provides graphical results of pot assays conducted to assess the mortality of Dermolepida achieved by *H. zealaiidica* strains JB1/X1, JB1/Q and NZH3 and *Steinernema glaseri* strain NC34.

Figure 5:
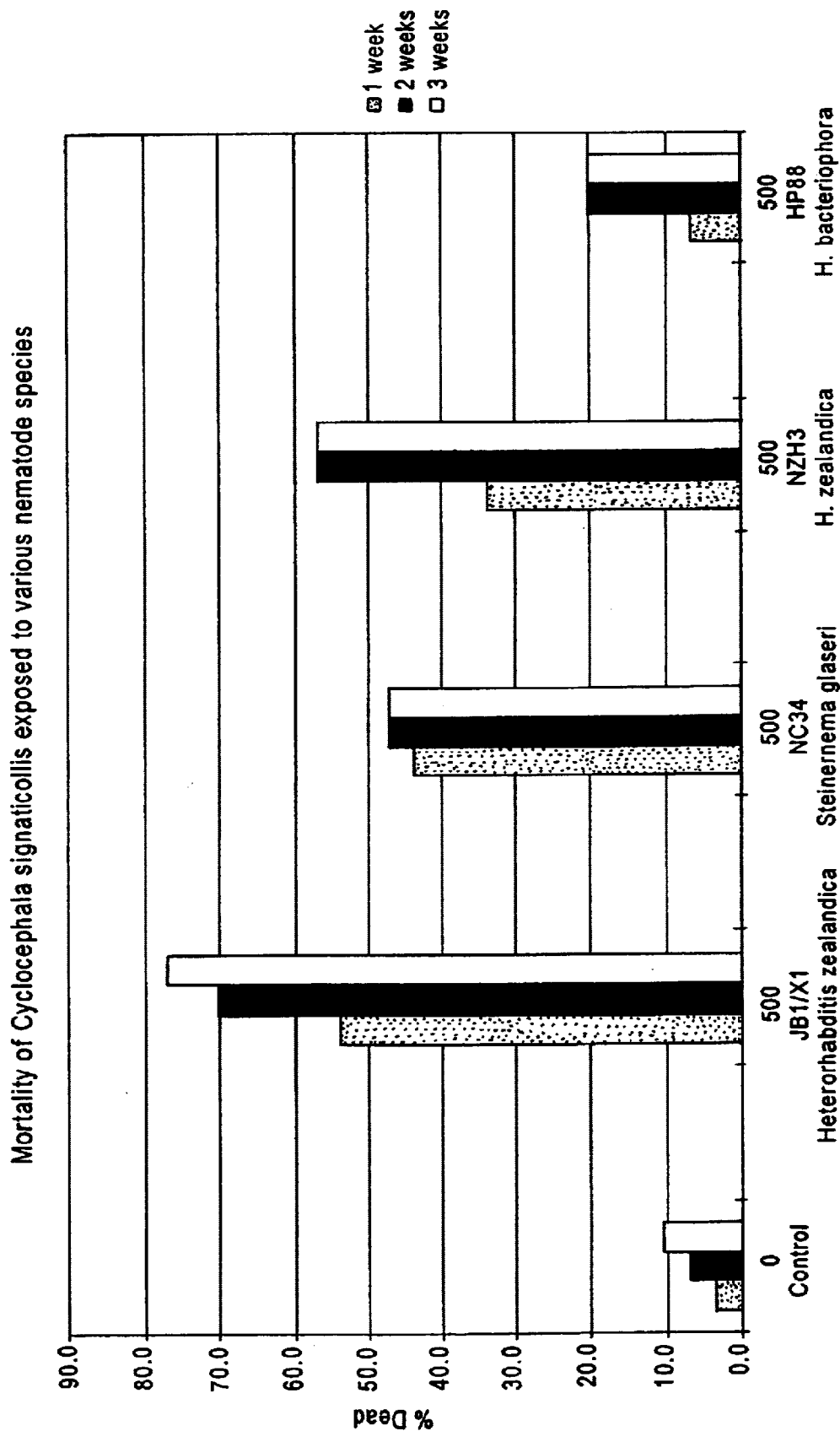

FIG. 5 provides graphical results of pot assays conducted to assess the mortality of *C. siguaticoilis* achieved by *H. zealandica* strains JB1/X1 and NZH3, *S. glaseli* strain NC34 and *H. bacteriophora* HP88.

Figure 6:
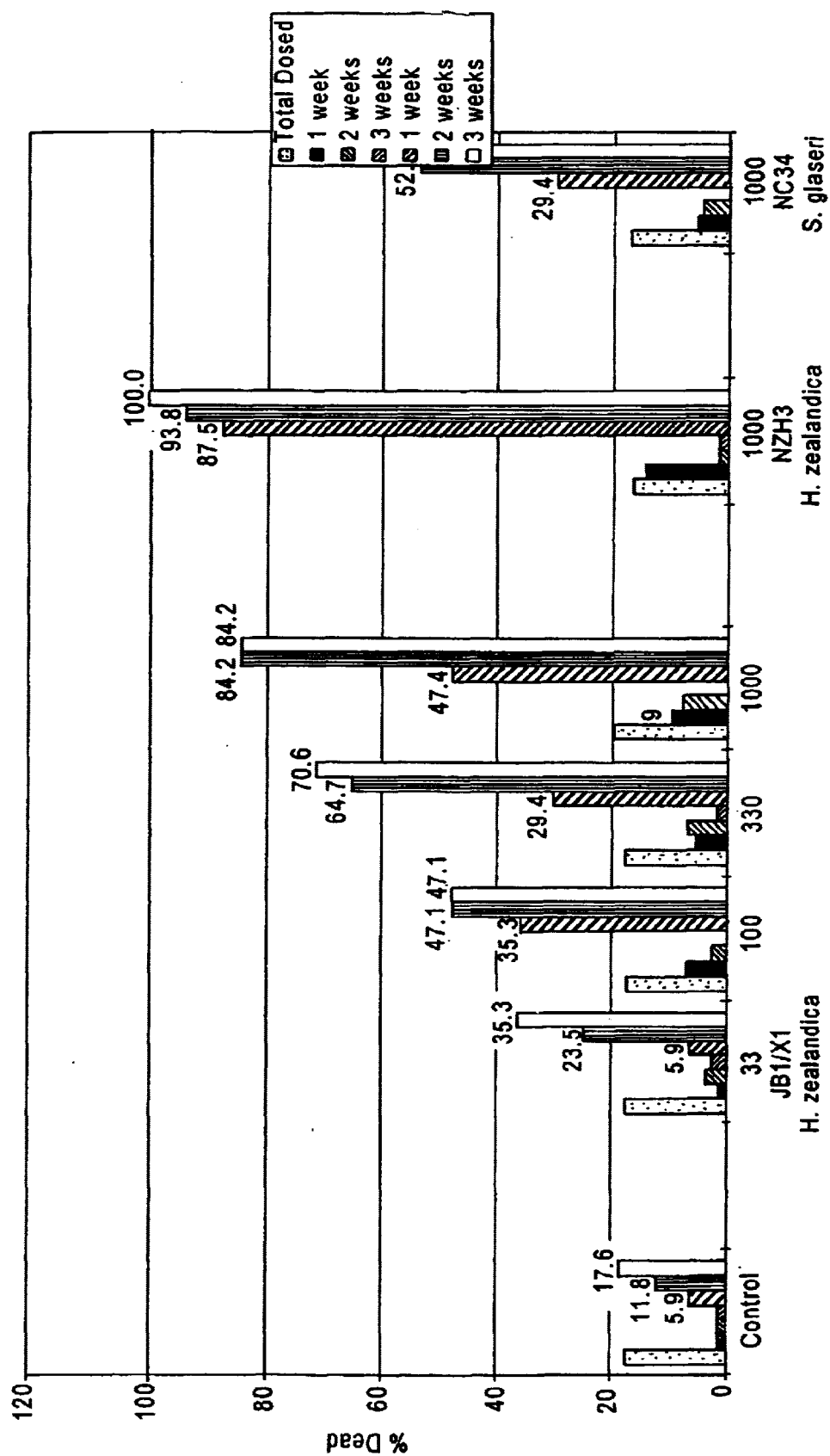

FIG. 6 provides graphical results of pot assays conducted to assess the mortality of *A. parvulus* achieved by *H. zealandica* strains JB1/X1 (Per 100, 330 and 100 nematodes) and NZH3, and *S. glaseri* strain NC34.

FIG. 7 provides graphical results of pot assays conducted to assess the mortality of *L. negatoria* achieved by *H. zealandica* strain JB1/X1 and *S. glaseri* strain NC34.

FIG. 8 provides graphical results to assess the mortality of adult *H. arator* achieved with *H. zealandica* strains JB1/X1, NZH3 and Botany, *S. glaseri* strain NC34, *S. feltiae* and *S. carpocapsae* BW.

FIG. 9 provides graphical results of studies conducted to deterimne LD50s of *H. zealandica* strains in pot assays against final instar *C. signaticollis*.

FIG. 10 provides graphical results in field trials of *Heterorhabditis zealandica* X1 against African black beetle scarab.

EXAMPLE 1

Isolation and Characterisation of *H. zealandica* Nematodes

Soil samples infested with nematodes were collected from a number of field sites throughout Australia. Using the method of Bedding and Akhurst (1975), nematodes were isolated and subsequently assigned to a species on the basis of morphological characterisation (see Wouts (1979)) and DNA analysis (see Tables 1 and 2). Eight of the isolated nematodes were assigned to the species *H. zealazidica*.

Samples of three of the *H. zealandica* strains, namely JB1/X1, GKB and JB3D were deposited under the Budapest Treaty with the Australian Government Analytical Laboratories (AGAL), P.O. Box 385, Pymble, New South Wales 2073, Australia. These deposits have been accorded the Accession Nos. 10726, 10727 and 10728, respectively.

Random Amplificatioii of Polymorphic DNA (RAPD) studies were conducted on DNA from the *H. zealandica* nematodes in accordance with the method of Hashmi, Glazer and Gangler (1996). The results which are presented in FIGS. 1–3, indicate that various of the strains may be seperated on the basis of their RAPD patterns (e.g. strains JB1/X1 and JB3D can be distinguished on the basis of their RAPD pattern obtained with the prilner OP-X11).

TABLE 1

Percentage Similarity of Domain 3 DNA Sequences of Heterorhabditis Strains. (299 bp Region)

|  | NZH3 | Windsor | JBX1 | JBQ1 | WA Het | Irish M145 | HT390 | Microbio | NJ | C1 |
|---|---|---|---|---|---|---|---|---|---|---|
| NZH3 | 100 | | | | | | | | | |
| Windsor | 100 | 100 | | | | | | | | |
| JBX1 | 100 | 100 | 100 | | | | | | | |
| JBQ1 | 100 | 100 | 100 | 100 | | | | | | |
| WA Het | 100 | 100 | 100 | 100 | 100 | | | | | |
| Irish M145 | 98.67 | 98.67 | 98.67 | 98.67 | 98.67 | 100 | | | | |
| HT390 | 98.67 | 98.67 | 98.67 | 98.67 | 98.67 | 100 | 100 | | | |
| Microbio | 98.33 | 98.33 | 98.33 | 98.33 | 98.33 | 99.67 | 99.67 | 100 | | |
| NJ | 94.98 | 94.98 | 94.98 | 94.98 | 94.98 | 96.32 | 96.32 | 95.99 | 100 | |
| C1 | 94.65 | 94.65 | 94.65 | 94.65 | 94.65 | 95.99 | 95.99 | 94.98 | 99.00 | 100 |

Known comparative strains: NZH3 (*H. zealandica*), Microbio (*H. megidis*), Irish M145 ("Irish Megidis"), NJ & C1 (*H. bacteriophora*). Deletions have been included as base pair changes.

TABLE 2

Percentage Similarity of Internal Transcribed Spacer 1 DNA Sequences of Heterorhabditis Strains. (805 bp Region)

|  | NZH3 | Windsor | JBX1 | JBQ1 | WA Het | Irish M145 | HT390 | *H. hepialus* | *H. marelatus* | Microbio |
|---|---|---|---|---|---|---|---|---|---|---|
| NZH3 | 100 | | | | | | | | | |
| Windsor | 100 | 100 | | | | | | | | |
| JBX1 | 99.88 | 99.88 | 100 | | | | | | | |

TABLE 2-continued

Percentage Similarity of Internal Transcribed Spacer 1 DNA Sequences of Heterorhabditis Strains. (805 bp Region)

|             | NZH3  | Windsor | JBX1  | JBQ1  | WA Het | Irish M145 | HT390 | H. hepialus | H. marelatus | Microbio |
|-------------|-------|---------|-------|-------|--------|------------|-------|-------------|--------------|----------|
| JBQ1        | 99.88 | 99.88   | 100   | 100   |        |            |       |             |              |          |
| WA Het      | 99.88 | 99.88   | 100   | 100   | 100    |            |       |             |              |          |
| Irish M145  | 89.07 | 89.07   | 89.19 | 89.19 | 89.19  | 100        |       |             |              |          |
| HT390       | 88.57 | 88.57   | 88.70 | 88.70 | 88.70  | 94.78      | 100   |             |              |          |
| H. hepialus | 81.80 | 81.80   | 81.80 | 81.80 | 81.80  | 91.24      | 99.31 | 100         |              |          |
| H. marelatus| 81.57 | 81.57   | 81.57 | 81.57 | 81.57  | 91.01      | 99.08 | 99.77       | 100          |          |
| Microbio    | 84.97 | 84.97   | 85.09 | 85.09 | 85.09  | 93.66      | 89.69 | 87.56       | 87.33        | 100      |

Known comparative strains: NZH3 (*H. zealandica*), Microbio (*H. megidis*), Irish M145 ("Irish Megidis"). *H. marelatus* and *H. hepialus* sequences were extracted from Genbank and their comparisons are based on a 434 bp overlap of the 805 bp ITS1 region. Deletions have been included as base pair changes.

EXAMPLE 2

Control of Scarabs with *H. zealandica* Nematodes

A variety of trials were conducted with several strains of *H. zealandica* and other nematodes against scarabs. Laboratory based trials included a comparison of strains by dosing a homogeneous selection of larvae with an equivalent number of nematodes of each strain and assessing the number of larvae killed (see Comparison Trials), and the determination of LD50s from pot assays against final instar *Cycoceplhala signaticollis* (see LD50 Trials).

Comparison Trials

1. Dermolepida

Pot assays using the method of Bedding, Molyneux and Akhurst (1983) (see LD50 Trials), were conducted using final instar larvae of Dermolepida dosed with *H. zealandica* strains JB1/X1 and JB1/Q. JB1/X1 achieved 70% kill while JB1/Q had little effect (at 1000 IJs/pot). Subsequent experiments with the above strains as well as *H. zealandica* NZH3 and *S. glaseri* NC34 at the same dose (see FIG. 4) showed that JB1/X1 achieved superior kill (over 90% kill after 3 weeks with JB1/X1 versus 57% after 3 weeks with *S. glaseri* NC34, being the best of the others). Control mortality was too high in tests done on first instar larvae to give a valid result.

2. Cyclocephala

Pot assays were conducted on final instar *C. signaticollis* larvae with the NC34 strain of *S. glaseri*, *H. bacteriophora* HP88 and the NZH3 and JB1/X1 strains of *H. zealandica* (at 500 Ijs/pot). The results obtained (see FIG. 5) showed that JB1/X1 achieved superior kill. Subsequent assays comparing JB1/X1 with a range of other strains of *H. zealandica* (namely, JB3/D, Botany, GKA, GKB, GKC and JB3/F) at a dose of 200 IJs/pot showed JB1/X1 to equal (JB3/D, Botany, GKB and GKC) or superior (B3/F and GKA) in killing power. In addition, pot assays comparing JB1/X1 to a range of field collected material at 200 IJs/pot (niamiely, JB4/A to JB4/E, Qld CS9, and JB4/H, all of which are *H. zealandica*), JB1/X1 was again found to achieve superior kill.

3. *Antitrogus parvulus*

Pot assays were conducted on final instar *Antitrogus parvulus* comparing *H. zealandica* strains JB1/X1 and NZH3 and *S. glaseri* strain NC34. The results (see FIG. 6) showed that NZH3 achieved the best kill particularly in the short term. Further, NZH3 achieved close to its maximum level of control in one week whereas JB1/X1 required two weeks. Subsequent assays using a lower dose (500 instead of 1000) resulted in all of *H. megidis* strain MicroBio *H. bacteriophora* strain HP88 and *H. zealandica* strains JB1/X1 and NZH3 achieving a very poor level of kill.

4. *Lepidiota negatoria*

Pot assays were conducted on final instar *Lepidiota negatoria* comparing *H. zealandica* strain JB1/X1 and *S. glaseri* strain NC34. The results (see FIG. 7) showed that JB1/X1 achieved over 80% kill with 100 nematodes per larvae after 2 weeks, whereas NC34 achieved only 35% kill with 1000 nematodes after the same period.

5. *Heteronychus arator*

Pot assays were conducted on adult *Heteronychus arator* (African Black Beetle) comparing *H. zealandica* strains JB1/X1, NC34, NZH3 and Botany, *S. feltiae*, and *S. carpocapsae* BW at 1000 IJs/pot. The results (see FIG. 8) showed that BW achieved some control while the others were ineffective.

6. *Xylotrupes gideon*

Preliminary studies have showed that the *H. zealacidica* strain JB1/X1 at a dose of 1000 IJs/pot, is capable of killing *Xylotrupes gideon* larvae.

7. Anoplognathus sp.

Preliminary studies have showed that the *H. zealandica* strain JB1/X1 at a dose of 1000 IJs/pot, is capable of killing Anoploplognathus species.

LD50 Trials with *C. signaticollis*

Assays to determine the LD50s of the *H. zealandica* strains Windsor, JB1/X1, GKB, NZH3, GKA, JB6, JB3/D and HT390 (H. sp) against freshly collected final instar *C. signaticollis* were conducted in accordance with the following method:

*C. signaticollis* larvae (collected from a playing field at the Australian National University, Canberra, Australian Capital Territory) were exposed individually to nematodes within plastic screw-cap specimen jars (diameter 4.2 cm, height 6 cm) filled to within 1 cm of the top with approximately 80 g of fine sand, moisture content to about 7% (pF=1.3). The larvae were placed at the bottom of the jars. Nematodes were introduced in 1 ml of water into a centrally placed well at the top (0.5 cm diameter, 2 cm deep), which was then filled with sand. Numbers of nematodes were estimated by dilution counts. There were 20 applications of each dosage for each nematode strain. After 14 days incubation at a temperature of 23 degrees C. larvae were removed and if dead were dissected and microscopically examined for neatode infection in the insect Ringers solution. The LD50 values were computed using the probit analysis of Finney 1971.

The results are shown in FIG. 9. In particular, FIG. 9 shows the level of kill achieved by each strain at a range of doses (corrected for control mortality).

These results allowed the calculation of LD50s against *C. signaticollis* as follows in Table 3:

LD50 and LD90 and confidence limits were calculated using the probit analysis and Fieller procedures in Genstat 5.

TABLE 3

LD50s of various strains of *Heterorhabditis zealandica* against final instar *Cyclocephala signaticollis*

| Strain | LD50 | 95% | Limits | Strain | LD90 | 95% | Limits |
|---|---|---|---|---|---|---|---|
| JB3/D | 110 | 57 | 222 | JB3/D | 739.7 | 315.7 | 14430 |
| JB1/X1 | 121 | 65 | 203 | JB1/X1 | 848.7 | 430.8 | 3708 |
| WINDSOR | 148 | 83 | 250 | WINDSOR | 10004 | 506.4 | 4384 |
| GKB | 230 | 109 | 444 | GKB | 3755 | 1473 | 28650 |
| NZH3 | 596 | 340 | 1052 | NZH3 | 4339 | 2062 | 22781 |
| GKA | 562 | 286 | 1094 | GKA | 6041 | 2427 | 63009 |
| JB6 | 3170 | 1194 | 47424 | JB6 | 122652 | 15096 | 199788676 |
| HT390 | 4831 | 1064 | 2E+08 | HT390 | 65842 | 9024 | 1.29E+20 |

LD50s and LD90s and confidence limits calculated using the probit analysis and Fieller procedures in Genstat 5

LD50 Trials with Other Scarab Species

LD50s of *H. zealandica* strain JB1/X1 against other species of scarabs (i.e. the Japanese beetle, *P. japonica*) may be determined by the following method.

1. Scarab larvae are exposed individually to nematodes within plastic screw cap specimen jars (diameter 4.2 cm, height 6.0 cm) filled to within one cm of the top with 80 g of clean, fine sand carefully mixed with water to achieve an eveii moisture content of 7% (Pf=1.3). A larval scarab is placed at the bottom of each specimen jar, sand lightly packed over it and the top screwed on tigltly.
2. Nematodes are introduced in 1 ml of water into a centrally placed well (0.5 cm diameter, 2 cm deep), which is then filled with sand.
3. Five dosages of IJs are each applied to 20 scarab larvae with a further 40 larvae as controls (total of 140 larvae). The dosages used are 10, 33, 100, 330, and 1000 IJ/ml.
4. Larvae are examined after one week and two weeks at 23 degrees C. with live and dead recorded on both occasions.
5. LD50s are calculated using the probit analysis and Fieller procedures within the software package, Genstat 5 (Genstat 5, Release 4.1, Third Edition, Lawes Agicultural Trust, (IACR-Rothamsted), 1997).

Tables 4 and 5 provides the results of LD50s of *H. zealandica* against various scarab species using the above method.

TABLE 4

LD50s and LD90s of various scarabs after 2 weeks exposure to *H. zealandica* JB1/X1

| Scarab Species | | 95% | Limits |
|---|---|---|---|
| | LD50 | | |
| Adoryphorus couloni | 128 | 74 | 228 |
| Lepidiota negatoria | 177 | 85 | 317 |
| Antitrogus parvulus | 186 | 75 | 449 |
| Cyclocephala signaticollis | 121 | 65 | 203 |
| Popillia japonica | 115.6* | 75 | 181 |
| | LD90 | | |
| Adoryphorus couloni | 1396 | 627 | 6486 |
| Lepidiota negatoria | 964 | 438 | 6810 |
| Antitrogus parvulus | 3402 | 1009 | 227541 |
| Cyclocephala signaticollis | 848.7 | 430.8 | 3708 |
| Popillia japonica | 1174* | 871 | 5742 |

*from pooled data

TABLE 5

LD50 results from tests on *Popillia japonica*

| | | Lower 95% | Upper 95% |
|---|---|---|---|
| Rep 1 | LD50 | | |
| After 1 week | 5236 | 681.1 | 3.94E + 18 |
| After 2 week | 182.3 | 95.42 | 410.9 |
| Rep 2 | LD50 | | |
| After 1 week | 147.9 | 86.81 | 265.9 |
| After 2 week | 76.38 | 41.01 | 134.9 |
| Pooled reps | LD50 | | |
| After 1 week | 412.7 | 233.2 | 993.7 |
| After 2 week | 115.6 | 74.81 | 180.8 |
| | LD90 | | |
| After 2 weeks | 1174 | 871 | 5742 |

EXAMPLE 3

Effectiveness of *H. zlalandica* Nematodes Against Various Scarabs in the Field

Small scale field trials were conducted by treating small turfed areas, followed by periodic "digging uip" to count live and dead scarabs and larvae.

1. One trial was made during February 1999 at the Peninsula Golf Club in Victoria (Australia) where there was a heavy infestation of black beetle *H. arator*, larvae. Four turfed area of 10 m$^2$ were treated with *H. zealandica* JB1/X1 at an amount of 250,000 IJ/m$^2$ as part of a random block design including various other treatments. Observations revealed that 50% of larvae in the treated area were killed after two weeks and 80% after three weeks (see FIG. 10), whereas there was negligible neinatode death in the control plots. Separate from this trial, the golf club superintendent treated larger areas of turf (about 2 hectares) with only 100,000 IJ/m$^2$ and found no bird feeding damage in the treated area but significant damage nearby.
2. In a second trial, 500,000 IJ/m$^2$ were sprayed over 100 m$^2$ of a Canberra soccer field (Australian Capital Territory) heavily infested with Argentine scarab, *C. signaticollis*. After eight days, 33% of the nemiatodes were dead, after 23 days 52%, and after thirty days 61% were dead over six sample areas but only 3% were dead in ain area of dry soil. After 68 days no scarabs were found alive and 16 dead in thirteen 200 cm² samples of treated area whereas 18 live larvae were found in untreated areas.

3. Small areas in two Canberra back garden lawns (Australian Capital Territory) with very lush grass and severe infestations of *C. signaticollis* were treated with *H. zealandica* at one million IJ/m². In the first garden, after 11 days, there were 30% nematodes dead in one plot and after 35 days, 74% nematode death in one plot with 90% death in another (based on only 19 and 11 larvae respectively). In the second garden, no dead scarabs could be found after 20 days, but after 40 days a total of 42 dead and 4 live scarabs (91%) were found in samples of three plots.

4. In late February 1999, 4 areas of turf within a quadrangle at the Australian National University (Australian Capital Territory) were treated with *H. zealandica* at 500,000 IJ/m². After two weeks there was a little nematode death, after three weeks all average of 48% nematode death over three plots, after 4 weeks 81%, and after six weeks 90% nematode death.

The results above indicate that certain strains of *H. zealandica* may be used as biological control agents for scarabs. Since *H. zealandica* nematodes may be readily and cost-effectively reared using solid culture as described by Bedding (1981, 1984); their use in liquid or solid compositions would appear to offer a viable alternative to lawn scarab control by chemical pesticide spraying.

References

1. BEDDING, R. A. (1981). Low cost in vitro mass production of Neoaplectana and Heterorhabditis species (Nematoda) for field control of insect pests. *Nematologica* 27: 109–14.
2. BEDDING, R. A. (1984). Large scale production, storage and transport of the insect parasitic nematodes Neoaplectana spp. and Heterorhabditis spp. *Ann. appl. Biol.* 104: 117–120.
3. BEDDING, R. A. AND AKHURST, R. J. (1975). A simple technique for the detection of insect parasitic rhabditid nematodes in soil. *Nematologica* 21: 109–10.
4. BEDDING, R. A., MOLYNEUX, A. S. AND AKHURST, R. J. (1983). Heterorhabditis spp., Neoaplectana spp. and *Steinernema Kraussei*: Interspecific and intraspecific differences in infectivity for insects. *Experimental Parasitology* 55: 249–57.
5. BEDDING R. A., M. S. STANFIELD, AND G. W. CROMPTON (1991). Apparatus and Method for Rearing Nematodes, Fungi, Tissue Cultures and The Like, and For Harvesting Nematodes. International Patent Application No PCT/AU91/00136.
6. HASHMI, G., GLAZER, I. & GAUGLER, R. (1996). Molecular comparisons of entomnopathogenic nematodes using Random amplified Polymorphic DNA (RAPD) markers. *Fundam. appl. Nematol.*, 18:55–61.

SEQUENCE LISTING

<160> NUMBER OF SEQ ID NOS: 3

<210> SEQ ID NO 1
<211> LENGTH: 10
<212> TYPE: DNA
<213> ORGANISM: Heterorhabditis zealandica

<400> SEQUENCE: 1
aatcgggctg                                                                10

<210> SEQ ID NO 2
<211> LENGTH: 10
<212> TYPE: DNA
<213> ORGANISM: Heterorhabditis zealandica

<400> SEQUENCE: 2
cctgatcacc                                                                10

<210> SEQ ID NO 3
<211> LENGTH: 10
<212> TYPE: DNA
<213> ORGANISM: Heterorhabditis zealandica

<400> SEQUENCE: 3
ggagcctcag                                                                10

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A composition comprising an amount of an entomopathogenic nematode selected from the group of *H. zealandica* strains consisting of strains JB1/X1, GKB and JB3D, optionally in admixture with a suitable agricultural and/or horticultural carrier.

2. The composition of claim 1, wherein the amount of the entomopathogenic nematode is an amount in the range of about 50 to 10,000 nematodes/ml of composition.

3. The composition of claim 2, wherein the amount of the entomopathogenic nematode is an amount in the range of about 500 to 10,000 nematodes/ml of composition.

4. A method for controlling a population of larval and/or pupal scarabs in an affected area, said method comprising applying to said area a composition in accordance with claim 1, thereby the population of the larval and/or pupal scarabs is controlled.

5. The method of claim 4, wherein the composition is applied to the affected area so as to provide a dose of 50,000 to 1,000,000 IJ/m$^2$.

6. The method of claim 5, wherein the composition is applied to the affected area so as to provide a dose of 100,000 to 500,000 IJ/m$^2$.

7. The method of claim 4, wherein the composition is applied to the affected area at dusk.

8. The method of claim 4, wherein the method is for controlling a population of larval and/or pupal scarabs selected from the group of scarab species consisting of *Cyclocephala signaticollis, Heteronychus arator, Adoryphorus couloni, Antitrogus morbillosus, Anoplognathus porosus, Ataenius imparalis, Sericesthis geminata, S. pruinosis, S. nigrolineata, Scityla sericans, Saulostomus villosus, Aphodius tasmaniae*, Heteronyx spp, *Rhopoea magnicornis, Popillia japonica, Cyclocephala borealis, C. hirta, C. parallela, Melolontha melolontha, Anomala aenea, Phyllophaga phyllophaga, P. hirticula, Phyllopertha horticola, Haplididia etrusca, Maladea matrida, Costelytra zealandica, Amphimallon solstatialis* and *Ligyrus subtropicus*.

9. The method of claim 8, wherein the method is for controlling a population of larval and/or pupal scarabs of the species of *C. signaticollis*.

10. The method of claim 8, wherein the method is for controlling a population of larval and/or pupal scarabs of the species of *P. japonica*.

11. An isolated nematode selected from the *H. zealandica* strains designated JB1/X1, GKB and JB3D.

12. A process for producing a composition for controlling larval and/or pupal scarabs comprising:

(i) subjecting one or more candidate entomopathogenic nematodes of the species *Heterorhabditis zealandica* to a 14-day pot assay against final instar *Cyclocephala signaticallis* larvae and/or final instar *Popilla japonica* larvae;

(ii) selecting an entomopathogenic nematode which has an LD$_{50}$ value of less than 300 IJ as measured by the 14-day pot assay; and (iii) admixing the entomopathogenic nematode of step (ii) with a suitable agricultural or horticultural carrier.

13. The process of claim 12 wherein the entomopathogenic nematode is a strain of *H. zealandica* which has an LD$_{50}$ value of less than 175 IJ as measured by the 14-day pot assay against final instar *C. signiticollis* larvae and/or final instar *P. japonica* larvae.

14. The process of claim 12 wherein the entomopathogenic nematode is selected from the group of *H. zealandica* strains consisting of strains JB1/X1, GKB and JB3D.

15. The process of claim 12 wherein the amount of the entomopathogenic nematode admixed with the carrier is in the range of about 50 to 10,000 nematodes/ml.

16. A method for controlling a population of larval and/or pupal scarabs in an affected area, said method comprising applying to said area a composition produced in accordance with claim 12, thereby the population of the larval and/or pupal scarabs is controlled.

17. The method of claim 16 wherein the composition is applied to the affected area so as to provide a dose of 50,000 to 1,000,000 IJ/m$^2$.

18. The method of claim 16 wherein the composition is applied to the affected area at dusk.

19. The method of claim 16 wherein the method is for controlling a population of larval and/or pupal scarabs selected from the group of scarab species consisting of *Cyclocephala signaticollis, Heteronychus arator, Adoryphorus couloni, Antitrogus morbilliosis, Anagplognathus porosus, Ataenius imparalis, Sericesthis geminant, S. pruinosis, S. noigrolineata, Scityla sericans, Saulostomus villosus, Aphodius tasmaniae*, Heteronyx spp, *Rhopoea magnicornis, Popillia japonica, Cyclocephala borealis, C. hirta, C. parallela, Melolontha melolontha, Anomala aenea, Phyllophaga phyllophaga, P. hirticula, Phyllophertha horticola, Haplididia etrusca, Maledea matrida, Costelytra zealandica, Amphimallon solstatialis*, and *Lygyrus subtropocus*.

* * * * *